United States Patent [19]

Clemence et al.

[11] Patent Number: 4,968,700
[45] Date of Patent: Nov. 6, 1990

[54] 8-AMINO DECAHYDROQUINOLINES HAVING CENTRAL NERVOUS SYSTEM ANALGESIC ACTIVITY

[75] Inventors: Francois Clemence; Michel Fortin; Odile Le Martret, all of Paris; Francoise Delevallee, Fontenay sous Bois, all of France

[73] Assignee: Roussel Uclaf, Paris, France

[21] Appl. No.: 217,834

[22] Filed: Jul. 11, 1988

Related U.S. Application Data

[62] Division of Ser. No. 2,778, Jan. 13, 1987, Pat. No. 4,816,465.

[30] Foreign Application Priority Data

Jan. 13, 1986 [FR] France ............... 86 00354

[51] Int. Cl.$^5$ ............... A61K 31/47; C07D 217/00
[52] U.S. Cl. ............... 514/311; 514/314; 546/164
[58] Field of Search ............... 546/164; 544/128, 363; 514/311, 314, 256, 227, 235.2

[56] References Cited

U.S. PATENT DOCUMENTS

| | | | |
|---|---|---|---|
| 3,991,065 | 11/1976 | Curran et al. | 546/171 |
| 4,145,435 | 3/1979 | Szmuszkovicz | 544/399 |
| 4,173,636 | 11/1979 | Prost | 546/162 |
| 4,359,476 | 11/1982 | Kaplan et al. | 546/230 |
| 4,845,099 | 7/1989 | Rüger et al. | 514/314 |

FOREIGN PATENT DOCUMENTS

| | | | |
|---|---|---|---|
| 0258095 | 3/1988 | European Pat. Off. | 546/164 |
| 2617164 | 12/1988 | France | 546/164 |
| 39-4481 | 4/1964 | Japan | 544/128 |

Primary Examiner—Mukund J. Shah
Assistant Examiner—E. C. Ward
Attorney, Agent, or Firm—Bierman and Muserlian

[57] ABSTRACT

Novel enantiomeric and diastereoisomeric forms of decahydroquinolines of the formula

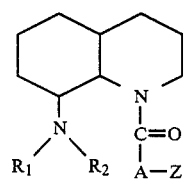

I wherein $R_1$ and $R_2$ are individually selected from the group consisting of hydrogen and alkyl of 1 to 5 carbon atoms or taken together with the nitrogen atom to which they are connected form a 5 to 6 member heterocycle optionally including another heteroatom and optionally substituted, A is selected from the group consisting of —$(CH_2)_n$— and alkylene substituted with an alkyl and having 2 to 8 carbon atoms, n is an integer from 0 to 5, Z is selected from the group consisting of optionally substituted phenyl, naphthyl indenyl, monocyclic heterocycle of 5 to 6 members and a bicyclic heterocycle all being unsubstituted or substituted by one or more substituents and their non-toxic, pharmaceuically acceptable acid addition salts and quaternary ammonium salts having central analgesic properties.

6 Claims, No Drawings

8-AMINO DECAHYDROQUINOLINES HAVING CENTRAL NERVOUS SYSTEM ANALGESIC ACTIVITY

PRIOR APPLICATION

This application is a division of copending U.S. patent application Ser. No. 002,778 filed Jan. 13, 1987, now U.S. Pat. No. 4,816,465.

STATE OF THE ART

U.S. Pat. Nos. 4,145,435, 4,359,476 and 4,173,636 describe related compounds.

OBJECTS OF THE INVENTION

It is an object of the invention to provide the novel compounds of formula I and their acid addition salts and quaternary ammonium salts and a novel process and novel intermediates for their preparation.

It is another object of the invention to provide novel analgesic compositions and to provide a novel method of relieving pain in warm-blooded animals.

These and other objects and advantages of the invention will become obvious from the following detailed description.

THE INVENTION

The novel compounds of the invention are selected from the group consisting of enantiomeric and diastereoisomeric forms of decahydroquinolines of the formula

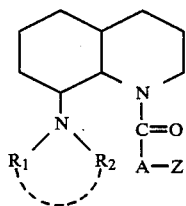

I wherein $R_1$ and $R_2$ are individually selected from the group consisting of hydrogen and alkyl of 1 to 5 carbon atoms or taken together with the nitrogen atom to which they are connected form a 5 to 6 member heterocycle optionally including another heteroatom and optionally substituted A is selected from the group consisting of —$(CH_2)_n$— and alkylene substituted with an alkyl and having 2 to 8 carbon atoms, n is an integer from 0 to 5, Z is selected from the group consisting of optionally substituted phenyl, naphthyl, indenyl, monocyclic heterocycle of 5 to 6 members and a bicyclic heterocycle all being unsubstituted or substituted by one or more substituents and their non-toxic, pharmaceutically acceptable acid addition salts and quaternary ammonium salts.

Examples of $R_1$ and $R_2$ are hydrogen, alkyl of 1 to 5 carbon atoms such as methyl, ethyl, n-propyl and isopropyl and isopropyl and heterocycles such as pyrrolidinyl, piperzinyl, piperidinyl and morpholinyl optionally substituted with alkyl or alkoxy of 1 to 5 carbon atoms.

Examples of Z are (a) phenyl unsubstituted or substituted with one or more substituents selected from the group consisting of alkyl and alkoxy of 1 to 5 carbon atoms, halogen, —OH, —$CF_3$, —$NO_2$, —$NH_2$ and mono- and dialkylamino of 1 to 5 alkyl carbon atoms and (b) naphtyl, indenyl or heterocyclic, all being unsubstituted or substituted with one or more substituents selected from the group consisting of alkyl and alkoxy of 1 to 5 carbon atoms, —$CF_3$, $NO_2$, $NH_2$, -mono- and dialkylamino of 1 to 5 alkyl carbon atoms and phenyl unsubstituted or substituted with one or more substituents selected from the group consisting of alkyl and alkoxy of 1 to 5 carbon atoms and halogen.

The alkyl and alkoxy and halogen substituents are preferably methyl, ethyl, n-propyl, isopropyl, n-butyl, branched butyl, methoxy, ethoxy, n-propoxy, isopropoxy, n-butoxy, branched butoxy, fluorine, chlorine, bromine and iodine. In the mono- and dialkylamino, the alkyl is preferably methyl or ethyl.

When Z is a monocyclic heterocycle, it is preferably thiazolyl, pyridinyl, oxazolyl, isoxazolyl, imidazolyl or thienyl.

Examples of A are —$(CH_2)_n$— wherein n is preferably 0 or 1 and alkylene substituted by alkyl such as 1,1-ethanediyl, 1-methyl-1,2-diethanediyl, 1-methyl-1,3-propanediyl, 2-methyl-1,3-propanediyl and 1-ethyl-1,2-ethanediyl.

The compounds of formula I can exist in the form of four racemates or pairs of enantiomers and the enantiomers of each pair can be separated by known processes.

Examples of suitable acids for the formation of non-toxic, pharmaceutically acceptable acid addition salts are inorganic acids such as hydrochloric acid, hydrobromic acid, nitric acid, sulfuric acid or phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and arylsulfonic acid such as benzenesulfonic acid.

Examples of quaternary ammonium salts of the compounds of formula I are those quaternized with compounds of the formula R—Y when R is alkyl of 1 to 4 carbon atoms such as methyl, ethyl, n-propyl or isopropyl and Y is a halide such as chloride, bromide or iodide.

Examples of preferred compounds of formula I are those wherein $R_1$ and $R_2$ are methyl or ethyl, those wherein $R_1$ and $R_2$ taken together with the nitrogen form pyrrolidinyl or pyridinyl, those wherein A is —$(CH_2)_n$— wherein n is 0 or 1, those wherein A is 1,1-ethanediyl, those wherein Z is phenyl, naphthyl, indenyl, pyridinyl, thienyl, thiazolyl, oxazolyl, isoxazolyl, imidazolyl, indolyl, quinolyl, benzofuranyl, benzo[b]thienyl, benzimidazolyl, benzoxazolyl, or benzothiazolyl, all optionally substituted and their non-toxic, pharmaceutically acceptable acid addition salts and their quaternary ammonium salts.

Among the more preferred compounds of formula I are those wherein $R_1$ and $R_2$ are methyl or ethyl or form pyrrolidinyl or pyridinyl with the nitrogen atom and A is 1,2-ethanediyl or —$(CH_2)_n$— when n is 0 or 1 and Z is phenyl, naphthyl, pyridinyl, thienyl, indolyl or benzo[b]thienyl, all optionally substituted and their non-toxic, pharmaceutically acceptable acid addition salts and quaternary ammonium salts.

Another preferred group of compounds of formula I are those wherein $R_1$ and $R_2$ and the nitrogen atom form pyrrolidinyl, A is 1,2-ethanediyl or —$(CH_2)_n$— and n is 0 or 1, Z is phenyl substituted with at least one halogen and/or —$CF_3$, naphthyl or benzo[b]thienyl and their acid addition salts and quaternary ammonium salts.

Specific preferred compounds of formula I are [4aRS(4aα, 8α, 8α) (±)decahydro-1-(3,4-dichlorophenyl)acetyl]-8-(1-pyrrolidinyl) quinoline, [4aRS(4aα,-8aα)]decahydro-1-[[4-(trifluoromethyl) phenyl]acetyl]-8-(1-pyrrolidinyl) quinoline, [4aRS(4aα,8α, 8aα)](±) decahydro-1-[4-(bromophenyl)-acetyl]-8-(1-pyrrolidinyl) quinoline, [4aRS(4aα, 8α,8aα)](±)decahydro-1-[2-(3,4-dichlorophenyl)-1-oxopropyl]-8-(1-pyrrolidinyl) quinoline, [4aRS(4aα, 8α, 8aα)](±)decahydro-1-(3,4-dichlorobenzyl)-8-(1-pyrrolidinyl)-quinoline, [4aRS(-4aα, 8α, 8aα)](±)-decahydro-1-[benzol[b]-thienyl)-acetyl]-8-(1-pyrrolidinyl)-quinoline and ]4aRS(4aα, 8α, 8aα)](±)-decahydro-1-[(1-naphthalenyl)-acetyl]-8-(1-pyrrolidinyl)-quinoline and their acid addition salts and quaternary ammonium salts.

The novel process of the invention for the preparation of the compounds of formula I comprises reacting 8-chloro-5,6,7,8-tetrahydroquinoline of the formula

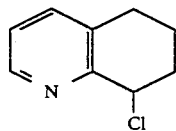

with an amine of the formula

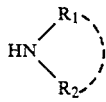

wherein R₁ and R₂ have the above definitions to obtain a compound of the formula

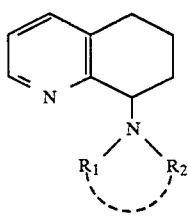

II reducing the latter to obtain a compound of the formula

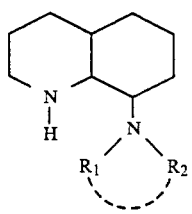

III reacting the latter with a compound or a functional derivative of a compound of the formula

IV wherein A and Z have the above definitions to obtain a compound of formula I in all the possible enantiomeric and stereo-isomeric forms, which is treated, if desired, with a mineral or organic acid to obtain an acid addition salt or with an alkyl halide to obtain a quaternary ammonium salt.

In a preferred mode of the process, when the compound of formula II is chemically reduced, the compounds of formula I are preferably obtained wherein the ring junction is trans and when the reduction is catalytical hydrogenation, the preferred ring junction is cis. A preferred chemical reducing agent is an alkali metal alcoholate such as sodium ethanolate and a preferred catalytic hydrogenation is effected with a platinium oxide catalyst.

The activation of the carboxyl function of the compound of formula IV to carry out the condensation with the compound of formula III is done in the presence of carbonyldiimidazole or dicyclohexylcarbodiimide. The acid of formula IV can also be activated in the form of an acid chloride or a mixed anhydride.

Furthermore, the two isomers corresponding to the α or β orientations of the group:

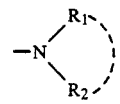

with respect to the ring may be separated by chromatography or by fractional crystallization of the salts for the products of formulae II and III. Each of the racemates obtained can be resolved by the usual methods, for example, by separation of the salts of the diastereoisomers obtained from optically active acids.

The novel analgesic compositions of the invention are comprised of an analgesically effective amount of at least one compound of formula I and their non-toxic, pharmaceutically acceptable acid addition salts and quaternary ammonium salts and an inert pharmaceutical carrier or excipient. The compositions may be in the form of tablets, dragees, capsules, granules, suppositories, injectable solutions or suspensions, ointments, creams, aerosols or gels prepared in the usual manner.

Examples of excipients are talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, and preservatives.

The compositions of the invention have a strong affinity for the opiate receptors and particularly for the K receptors and they are endowed with central analgesic properties as well as diuretic properties. Furthermore, certain of the compositions posses anti-arythmic, anti-ischemic and hypotensive properties.

The compositions are, therefore, useful for alleviating pain whatever its origin such as a pain of muscular, articular or nervous nature and are useful in the treatment of dental pains, migraines, shingles, in the treatment of intense pains, particularly those resistant to peripheral antalgics, for example in the course of neoplasia processes, in the treatment of pancreatitis, nephritic or biliary colics, in the treatment of post-operation and post-traumatic pains.

Among the preferred compositions of the invention are those wherein the active compound is selected from the group consisting of [4aRS(4aα, 8α, 8aα)](±)-decahydro-1-[(3,4-dichlorophenyl)-acetyl]-8-(1-pyrrolidinyl)-quinoline, [4aRS(4aα, 8α, 8aα)](±)-decahydro-1-[[4-(tri-fluoromethyl)-phenyl]-acetyl]-8-(1-pyrrolidinyl)-quinoline, [4aRS(4aα, 8α, 8aα)](±)-decahydro-1-[4-(bromophenyl)-acetyl]-8-(1-pyrrolidinyl)-quinoline, [4aRS(4aαα, 8α, 8aα)](±)-decahydro-1-[2-(3,4-dichlorophenyl) -1-oxopropyl]-8-(1-pyrrolidinyl)-quinoline, [4aα,8α, 8aα)](±)-decahydro-1-(3,4-dichlorobenzyl)-8-(1-pyrrolidinyl)-quinoline, [4aRS (4aα, 8α, 8aα)](±)-decahydro-1-[(benzo[b]-thienyl)-acetyl]-8-(1-pyrrolidinyl)-quinoline and [4aRS(4aα, 8α, 8aα)](±)-decahydro-1-[(1-naphthalenyl)-acetyl]-8-(1-pyrrolidinyl)-quinoline, as well as their acid addition salts and quaternary ammonium salts.

The novel method of the invention for relieving pain in warm-blooded animals, including humans, comprises administering to warm-blooded animals an analgesically effective amount of at least one compound of formula I and their non-toxic, pharmaceutically acceptable acid addition salts and quaternary ammonium salts. The compounds may be administered orally, rectally, parenterally or topically to mucosa and skin. The usual daily dose depends on the condition treated, method of administration and the specific compound. It can be from 0.25 to 5.5 mg/kg when the compound is administered orally and from 0.06 to 1.3 mg/kg when the compound is administered parenterally.

The compounds of formulae II and III are novel as well as 8-chloro-5,6,7,8-tetrahydroquinoline which may be prepared by chlorination of 5,6,7,8-tetrahydroquinoline-N-oxide according to the method indicated in U.S. Pat. No. 3,991,065.

In the following examples there are described several preferred embodiments to illustrate the invention. However, it is to be understood that the invention is not intended to be limited to the specific embodiments.

EXAMPLE 1

[4aRS(4aα,8α, 8aα)](±)-decahydro-1-[(3,4-dichlorophenyl)-acetyl]-8-(1-pyrrolidinyl)-quinoline hydrochloride STEP A: 8-chloro-5,6,7,8-tetrahydroquinoline hydrochloride At ambient temperature, 3 ml of methane sulfonyl chloride were added slowly to 1.49 g of 5,6,7,8-tetrahydroquinoline-N-oxide with stirring under an inert atmosphere. The mixture was heated for 4 hours at 80° to 82° C., then cooled to 20° C. and poured into 20 ml of a saturated solution of sodium bicarbonate. Then, sodium bicarbonate was added until an alkaline pH was obtained and after extracting with methylene chloride, washing with water, drying the re-united organic solutions and distilling to dryness under reduced pressure, 1.53 g of 8-chloro-5,6,7,8-tetrahydroquinoline was obtained in the form of an oil.

The above oil was dissolved in 2 ml of ethanol and 2 ml of a 5.75N solution in ethanol of hydrochloric acid were added. The hydrochloride crystallized out, and after diluting slowly at 20° to 25° C. with 4 ml of ether, the crystals were separated, rinsed first with a mixture of ethanol-ether (1-1) then with ether, and dried under reduced pressure at 20° C. After crystallization from ethanol, 0.893 g of the hydrochloride product melting at 240° C. were obtained.

STEP B: 8-pyrrolidinyl-5,6,7,8-tetrahydroquinoline

Over a period of 7 minutes with stirring and while allowing it to heat up, 50 ml of pyrrolidine were added to a solution of 20 g of 8-chloro-5,6,7,8-tetrahydroquinoline in 50 ml of water. The temperature reached 57° C. at the end of the introduction and stirring was continued for 1 hour at this temperature. The temperature was then allowed to return to 20° C. and the reaction medium was saturated with sodium chloride and then was extracted with other. The combined organic phases were dried and the solvents were eliminated under reduced pressure to obtain 20.22 g of 8-pyrrolidinyl-5,6,7,8-tetrahydroquinoline in the form of an oil.

STEP C: [4aRS(4aα, 8α, 8aα)[(±)-decahydro-8-(-pyrrolidinyl)-quinoline

This product is obtained mixed with other diastereoisomers by reduction of the product obtained in Step B either by catalytic hydrogenation or by a sodium-ethanol mixture. The description of these two reductions is given at the end of Example 4.

STEP D: [4aRS(4aα, 8α, 8aα)] (±)-decahydro-1-[(3,4-dichlorophenyl)-acetyl]-8-(1-pyrrolidinyl)-quinoline A solution of 873 mg of 3,4-dichlorophenyl-acetic acid and 690 mg of carbonyldiimidazole in tetrahydrofuran was stirred for 1 hour at 20° to 25° C. and then 645 mg of the product of Step C in solution in 3 ml of tetrahydrofuran was added. After stirring for 4 hours at ambient temperature, the tetrahydrofuran was eliminated under reduced pressure at less than 40° C. and the residue was taken up in 20 ml of ether. The solution was washed with a saturated solution of sodium bicarbonate, then with water saturated with sodium chloride and the ethereal phase was dried and distilled to dryness under reduced pressure to obtain 1.39 g of the crude product.

Preparation of the Hydrochloride 1.298 g of the product were dissolved in 5 ml of ether and the solution was filtered and rinsed with ether. 2 ml of ethanol were added to the filtrate and then 1.25 ml of a 5.75N solution in ethanol of hydrochloric acid was added until a pH of 1.2 was obtained. Crystallization was initiated, and after standing for 2 hours at 20° to 22° C., the crystals were separated, rinsed with a mixture of ethanol-ether (3-1) and then with ether. After drying under reduced pressure at 60° C., 852 mg of the hydrochloride were obtained. 825 mg of the latter were crystallized from ethanol to obtain 722 mg of the expected product melting at 233° C.

| Analysis: | | | | | | | | |
|---|---|---|---|---|---|---|---|---|
| Calculated: | 58.41 | % H | 6.77 | % N | 6.48 | % Cl | 24.63 |
| Found: | 58.7 | | 7.0 | | 6.5 | | 24.6 |

EXAMPLE 2

[4aRS(4aα, 8α, 8aα)](±)-decahydro-1-[(3,4-dichlorophenyl)-acetyl]-8-(1-pyrrolidinyl)-quinoline oxalate Using the procedure of Step D of Example 1, 876 mg of [4a RS (4aα, 8β, 8a α)](±)-decahydro-1-(3,4-dichlorophenyl)-acetyl]-8-(1-pyrrolidinyl)-quinoline (preparation given at the end of Example 4 were reacted to obtain 1.660 g of [4aRS(4aα, 8β, 8aα)](±)-decahydro-1-[(3,4-dichlorophenyl)-acetyl]-b 8-(1-pyrrolidinyl)-quinoline. After chromatographing over silica, (eluent:ethyl acetate with 1% of triethylamine), 316 mg of [4aRS(4aα, 8β, 8aα)](±)-decahydro-1-[(3,4-dichlorophenyl]-acetyl]-8-( 1-pyrrolidinyl)-quinoline melting at 90° C. were obtained.

Preparation of the Oxalate 280 mg of the said product were dissolved in 1.5 ml of 100% ethanol, filtered, rinsed with ethanol, and 130 mg of oxalic acid were added to the filtrate. The solution obtained were diluted slowly with 6 ml of ether and crystallization was initiated. After standing for one hour at ambient temperature, separating, and drying under reduced pressure at 65° C., 319 mg of product were obtained. 286 mg of the product were crystallized from ethanol to obtain 223 mg of the oxalate melting at 140° C. were obtained.

| Analysis: | | | | | | | | |
|---|---|---|---|---|---|---|---|---|
| Calculated: | % C | 54.34 | % H | 5.89 | % N | 5.28 | % Cl | 13.37 |
| Found: | | 54.5 | | 5.9 | | 5.4 | | 13.2 |

EXAMPLE 3

[4aRS(4aα, 8α, 8a β)] (±)-decahydro-1-[(3,4-dichlorophenyl)-acetyl)-8-(1-pyrrolidinyl)-quinoline A solution of 1.98 g of 3,4-dichlorophenyl acetic acid and 1.56 g of carbonyldiimidazole in 17 ml of tetrahydrofuran was stirred at 20° to 22° C., for one hour and then, 1,679g of [4aRS(4aα, 8α, 8aβ)](±)-decahydro-8-(1-pyrrolidinyl)-quinoline (preparation given at the end of Example 4) were added in solution in 5 ml of tetrahydrofuran. The solution was stirred for 4 hours at 20° to 22° C. and the tetrahydrofuran was eliminated under reduced pressure at less than 45° C. The residue was triturated in 15 ml of ether and in 5 ml of a saturated solution of sodium bicarbonate, then separated and rinsed, first with water than with ether. After drying under reduced pressure, 2.320 g of [4aRS(4αa, 8α,-8aβ)](±)-decahydro-1-[(3,4-dichlorophenyl)-acetyl]-8-(1-pyrrolidinyl)-quinoline melting at 138° C. were obtained.

Preparation of the Hydrochloride 2.309 g of the crude base were dissolved at reflux in 2 ml of ether and 2 ml of a 5.75N solution in ethanol of hydrochloric acid were added. After filtering hot, the product crystallized out on cooling of the filtrate. The crystals were separated, rinsed with ethanol and ether and dried under reduced pressure at 65° to 70° C. to obtain 1,816 g of the hydrochloride melting at 214° C.

| Analysis: | | | | | | | | |
|---|---|---|---|---|---|---|---|---|
| Calculated: | % C | 58.41 | % H | 6.77 | % N | 6.48 | % Cl | 24.63 |
| Found: | | 58.6 | | 6.8 | | 6.6 | | 24.6 |

EXAMPLE 4

[4aRS(4aα, 8β, 8aβ)](±)-decahydro-1-[(3,4-dichlorophenyl)-acetyl]-8-(1-pyrrolidinyl)-quinoline 1.384 g of the product were obtained by the procedure of Step D of Example 1 starting with 707 mg of [4aRS(4aα, 8β, 8aβ)](±)-decahydro-8-(1-pyrrolidinyl)-quinoline (preparation given at the end of Example 4). The oil obtained was then triturated in 10 ml of n-hexane. Crystallization was initiated followed by separating, rinsing with n-hexane and drying under reduced pressure at 20° C. to obtain 746 mg of [4aRS(4aα, 8β, 8aβ)](±)-decahydro-1-[(3,4-dichlorophenyl)-acetyl]-8-(1-pyrrolidinyl)-quinoline melting at 82° to 84° C.

Preparation of Fumarate

At 60° C., 817 mg of the said product were dissolved in 8 ml of ethanol and the solution was filtered and rinsed with boiling ethanol. 285 mg of fumaric acid were added to the filtrate and the mixture was refluxed with stirring. Crystallization took place on cooling and the crystals were separated, rinsed with ethanol and ether, then dried under reduced pressure at 70° C. to obtain 949 mg of the fumarate melting at 220° C.

| Analysis: | | | | | | | | |
|---|---|---|---|---|---|---|---|---|
| Calculated: | % C | 58.71 | % H | 6.31 | % N | 5.48 | % Cl | 13.86 |
| Found: | | 58.4 | | 6.3 | | 5.4 | | 13.7 |

Preparation of the 4 Following Diastereoisomers Used in Examples 1 to 4

[4aRS(4aα, 8α, 8aα)](±)-decahydro-8-(1-pyrrolidinyl)-quinoline=diastereo-isomer (cis A),

[4aRS(4aα, 8α, 8aα)](±)-decahydro-8-(1-pyrrolidinyl)-quinoline=diastereo-isomer (cis B),

[4aRS(4aα, 8α, 8aβ)](±)-decahydro-8-(1-pyrrolidinyl)-quinoline=diastereo-isomer (trans A),

[4aRS(4aα, 8α, 8aβ)](±)-decahydro-8-(1-pyrrolidinyl)-quinoline=diastereo-isomer (trans B).

These 4 diastereoisomers are obtained by reduction of the 8-pyrrolidinyl-tetrahydro-5,6,7,8-quinoline prepared in Step A of Example 1.

(1) Catalytic Reduction

A mixture of 6.24 g of 8-pyrrolidinyl-tetrahydro-5,6,7,8-quinoline, 62 ml of methanol 6.2 ml of hydrochloric acid and 690 mg of platinum oxide were introduced into a hydrogenating apparatus and hydrogenation was carried out at 22° to 25° C. at a pressure of 1850 mbars over 17 hours. The absorption of hydrogen lasted about 4 hours 30 minutes after which the catalyst was filtered off. After rinsing and distilling to dryness under reduced pressure, 8.67 g of reduction product were obtained.

(a) Crystallization of the Hydrochloride of the Diastereo-Isomer Cis A

The resin previously obtained was dissolved at 50° to 60° C. in 16 ml of isopropanol and crystallization was initiated at 20° C. After diluting with 12.5 ml of ether, the crystals were separated and rinsed with a mixture of isopropanol and ethyl ether (1-1), then with ether, and dried under reduced pressure at 50° C. The product obtained was crystallized from 42.5 ml of isopropanol with 2% of water and the crystals were separated, rinsed with isopropanol, then with ether to obtain 2.156 g of the expected product in the form of the hydrochloride melting at 210° C.

(c) Return to the Base 1 g of the hydrochloride was dissolved in 10 ml of water and 2 ml of 2N sodium hydroxide were added followed by extraction with ether, decanting, and washing with water saturated with sodium chloride. The ethereal solution was dried and distilled to dryness under reduced pressure to obtain 0.680 g of the expected product in the form of free base.

(c) Preparative Chromatography of the Mother-Liquors of Crystallization of the Hydrochloride of the Diastereo-Isomer cis A The mother-liquors of the crystallization of the hydrochloride of isomer cis A were combined and the return to the base was carried out in water and ethyl acetate by sodium hydroxide. After extraction, washing with water saturated with sodium chloride, drying and distilling to dryness under reduced pressure, chromatography was carried out on silica at ambient pressure. (eluent:ethyl acetate, 85—methanol 10—triethylamine 5) and the diastereoisomers cis B, trans A and cis A were recovered successively.

diastereoisomer cis B

The homogeneous elution fractions were evaporated to dryness under reduced pressure to obtain 2.059 g of the expected product.

diastereoisomer trans A

The following fractions were evaporated to dryness under reduced pressure to obtain 0.564 g of product. The hydrochloride was made and was crystallized from an ethanol-ether (1-1) mixture. The return to the base was carried out with 201 mg of hydrochloride in water, ether and 2N sodium hydroxide to obtain 139 mg of diastereoisomer trans A.

diastereoisomer cis A

The corresponding eluents were evaporated to dryness under reduced pressure to obtain 0.686 g of a brown resin which gave a hydrochloride melting at 210° C.

(2) Chemical Reduction

Under a pressure of 2.5 to 3 ml of mercury, a solution of 10.14 g of 8-pyrrolidinyl-tetrahydro-5,6,7,8-quinoline in 400 ml of ethanol was refluxed at 20° C. Then, over about 7 hours, 18 g of sodium were introduced in small portions at reflux. After returning to 20° C. under nitrogen, the mixture stood over night and then 14 g of sodium were introduced in small portions over 5 hours at reflux again. The reaction mixture was returned to 20° C. under nitrogen and poured into 400 ml of iced water with stirring. The ethanol was eliminated by distilling under reduced pressure at less than 50° C. and the residual medium was saturated with 28 g of sodium chloride. The mixture was extracted with ether and the ethereal phases were washed with water saturated with sodium chloride, dried and distilled to dryness under reduced pressure to obtain 6.68 g of the crude expected product in the form of a mixture.

After this a: preparation chromatography to separate the trans B, trans A and cis A diastereo-isomers was carried out. A chromatography was carried out over silica (eluent:ethyl acetate 85—methanol 10—triethylamine 5).

diastereo-isomer trans B

The fractions containing the first isomer were evaporated to dryness under reduced pressure to obtain 1.183 g of an oil and 1.163 g of this oil were dissolved in 2 ml of ethanol, filtered and rinsed with ethanol. The 830 mg of oxalic acid were added to the filtrate and the solution obtained was diluted slowly with 40 ml of ether while a precipitate formed. The supernatant solution was decanted and the gum was washed with ether and dissolved in 7 ml of water and 20 of ether. 2 ml of sodium hydroxide were added and the mixture was shaken in a flask and the decanted organic phase was washed with water saturated with sodium chloride. The etheral solutions were dried, rinsed and distilled to dryness under reduced pressure to obtain 1.010 g of the expected diastereoisomer trans B.

diastereoisomer trans A

Under reduced pressure, the homogeneous fractions from chromatography corresponding to the isomer trans A were evaporated to dryness to obtain 2.332 g of an oil and 2.322 g of this oil were dissolved in 2.5 ml of ethanol. The filtrate was diluted with 9.5 ml of ether, and 5 ml of a 5.75N solution of hydrochloric acid in ethanol were added. The hydrochloride obtained was separated, washed with a mixture of ethanol and ether (1- 1), then with ether and dried under reduced pressure at 60° C. to obtain 2.569 g of diastereo-isomer trans A in the form of the hydrochloride.

The return to the base was carried out by treating 2.464 g of the hydrochloride with 10 ml of water and 2 ml of 32% sodium hydroxide, then stirring, decanting and re-extracting with ether. The ethereal phases were washed with water saturated with sodium chloride, dried, and distilled to dryness under reduced pressure to obtain 1.679 g of the expected product.

diastereoisomer cis A

Under reduced pressure, the homogeneous fractions from chromatography corresponding to the diastereoisomer cis A were evaporated to dryness to obtain 0.579 g of the expected product which was dissolved in 5 ml of isopropanol. 2 ml of a 4.4M solution of dry hydrochloric acid in isopropanol were added and after diluting with 7 ml of ether, 0.15 ml of water were added, and crystallization was initiated. The crystals were separated, rinsed with a mixture of isopropanol—ether (1-1) and with ether, then dried under reduced pressure at 60° C. to obtain 504 mg of the cis A diastereoisomer B in the form of the hydrochloride melting at 210° C. The return to the base was carried out on 64 mg of the hydrochloride as indicated for the hydrochloride of the diastereoisomer trans A and 42 mg of the base were obtained.

EXAMPLE 5

[4aRS(4aα, 8α, 8aα](±)-1-[(4-chlorophenylacetyl]-decahydro-8-(1-pyrrolidinyl)-quinoline hydrochloride Using the procedure of Step D of Example 1, 554 mg of 4-chlorophenyl acetic acid, 527 mg of carbonyl diimidazole and 520 mg of the product obtained at Step B of Example 1 were reacted keeping the reaction medium stirred for 5 hour. After crystallization of the hydrochloride from a mixture of isopropanol and ether (1-1), 752 mg of [4aRS(4aα, 8α, 8aα)](±)-1-[(4-chlorophenylacetyl]-decahydro-8-(1-pyrrolidinyl)-quinoline hydrochloride were obtained melting at $\approx$ 222° C. (decomposes).

Analysis: $C_{21}H_{29}ClN_2O$, HCl; molecular weight = 397.391

| | % C | % H | % N | % Cl |
|---|---|---|---|---|
| Calculated: | 63.47 | 7.61 | 7.05 | 17.84 |
| Found: | 63.6 | 7.6 | 6.8 | 17.8 |

EXAMPLE 6

[4aRS(4aα, 8α, 8aα)](±)-1-[(4-trifluoromethyl)-phenyl]-acetyl]-decahydro-8-(1-pyrrolidinyl)-quinoline hydrochloride Using the procedure of Example 5, 663 mg of 4-trifluoromethylphenyl acetic acid were reacted with stirring for 16 hours. After crystallization of the hydrochloride from ethanol, 921 mg of [4aRS(4aα, 8α, 8aα)](±)-1-[(4-trifluoromethyl)-phenyl)-acetyl]-decahydro -8-(1-pyrrolidinyl)-quinoline hydrochloride melting at ≈208° C. (decomposes) were obtained.

Analysis: $C_{22}H_{29}F_3N_2O \cdot HCl$; molecular weight = 430.9447

|  | % C | % H | % N | % Cl | % F |
|---|---|---|---|---|---|
| Calculated: | 61.32 | 7.02 | 6.50 | 8.23 | 13.22 |
| Found: | 61.4 | 7.1 | 6.4 | 8.1 | 12.9 |

EXAMPLE 7

[4aRS(4aα, 8α, 8aα)](±)-1-[(4-bromophenyl)-acetyl]-decahydro-8-(1-pyrrolidinyl)-quinoline hydrochloride Using the procedure of Example 5, 699 mg of 4-bromophenyl acetic acid were reacted with stirring for 20 hours. After crystallization of the hydrochloride from isopropanol, 685 mg of [4aRS(4aα, 8α, 8aα)](±)-1-[(4-bromophenyl)-acetyl[-decahydro-8-(1-pyrrolidinyl)-quinoline hydrochloride melting at ≈235° C. (decomposes) were obtained.

Analysis: $C_{21}H_{29}BrN_2O$, HCl; molecular weight = 441.847

|  | % C | % H | % N | % Cl | % Br |
|---|---|---|---|---|---|
| Calculated: | 57.09 | 6.84 | 6.34 | 8.02 | 18.08 |
| Found: | 57.4 | 6.9 | 6.3 | 7.8 | 18.0 |

EXAMPLE 8

[4aRS(4aα, 8α, 8aα)](±)-1-[(4-nitrophenyl)-acetyl]-decahydro-8-(1-pyrrolidinyl)-quinoline hydrochloride Using the procedure of Step D of Example 1, 471 mg of p-nitrophenyl acetic acid, 422 mg of carbonyldiimidazole and 417 mg of the product prepared in Step C of Example 1 were reacted while maintaining stirring for 3 hours. After crystallization of the hydrochloride from ethanol, 606 mg of [4aRS(4aα, 8α, 8aα)](±)-1-[(4-nitrophenyl)-acetyl]-decahydro-8-(1-pyrrolidinyl)-quinoline hydrochloride melting at 249° C. (decomposes) were obtained.

Analysis: $C_{21}H_{29}N_3O_3$, HCl; molecular weight = 407.944

|  | % C | % H | % N | % Cl |
|---|---|---|---|---|
| Calculated: | 61.83 | 7.41 | 10.30 | 8.67 |
| Found: | 61.8 | 7.5 | 10.1 | 8.5 |

EXAMPLE 9

[4aRS(4aα, 8α, 8aα)](±)-1-[(3,4-dimethoxyphenyl)-acetyl]-decahydro-8-(1-pyrrolidinyl)-quinoline hydrochloride Using the procedure of Example 8, 510 mg of 3,4-dimethoxyphenyl acetic acid were reacted with stirring for 20 hours and 571 mg of [4aRs(4aα, 8α, 8a α)](±)-1-[(3,4-dimethoxyphenyl)-acetyl]-acetyl]-decahydro-8-(1-pyrrolidinyl)-quinoline hydrochloride melting at 250° C. (decomposes) were obtained.

Analysis: $C_{23}H_{34}N_2O_3$, HCl; molecular weight = 422.999

|  | % C | % H | % N | % Cl |
|---|---|---|---|---|
| Calculated: | 65.31 | 8.34 | 6.62 | 8.38 |
| Found: | 65.3 | 8.4 | 6.4 | 8.4 |

EXAMPLE 10

[4aRS(4aα, 8α, 8aα)(±)-1-[(2,4-dichlorophenyl)-acetyl]-decahydro-8-(1-pyrrolidinyl)-quinoline hydrochloride Using the procedure of Example 9, 533 mg of 2,4-dichlorophenyl acetic acid were reacted with stirring for 4 hours and [4aRS(4aα, 8α, 8aα)](±)-1-[(2,4-dichlorophenyl)-acetyl]-decahydro-8-(1-pyrrolidinyl)-quinoline hydrochloride melting at >260° C. were obtained.

Analysis: $C_{21}H_{28}Cl_2N_2O$, HCl; molecular weight = 431.836

|  | % C | % H | % N | % Cl |
|---|---|---|---|---|
| Calculated: | 58.41 | 6.77 | 6.48 | 24.63 |
| Found: | 58.7 | 6.8 | 6.5 | 24.6 |

EXAMPLE 11

[4aRS(4aα, 8α, 8aα)](±)-1-[(1-naphthalenyl)-acetyl]-decahydro-8-(1-pyrrolidinyl)-quinoline Using the procedure of Example 8, 484 mg of α-naphthyl acetic acid were reacted with stirring for 20 hours to obtain 769 mg of [4aRS(4aα, 8α, 8aα)](±)-1-[(1-naphthalenyl)-acetyl]-decahydro-8-(1-pyrrolidinyl)-quinoline melting at ≈262° C.

Analysis: $C_{25}H_{32}N_2O$, HCl; molecular weight = 413.007

|  | % C | % H | % N | % Cl |
|---|---|---|---|---|
| Calculated: | 72.70 | 8.05 | 6.78 | 8.58 |
| Found: | 72.9 | 8.2 | 6.8 | 8.7 |

EXAMPLE 12

[4aRS(4aα, 8α, 8aα)](±)-1-[2-(3,4-dichlorophenyl)-1-oxopropyl]-decahydro-8-(1-pyrrolidinyl)-quinoline hydrochloride (isomer A)

Using the procedure of Example 8, 482 mg of α-methyl-3,4-dichlorophenyl acetic acid, dl were reacted with stirring for 24 hours to obtain 334 mg of [4aRS(4α, 8α, 8a α)](±)-1-[2-(3,4-dichlorophenyl) -1-oxopropyl]-decahydro-8-(1-pyrrolidinyl)-quinoline hydrochloride (isomer A) MP=260° C. (decomposes).

| Analysis: $C_{22}H_{30}Cl_2N_2O$, HCl; molecular weight = 445.863 | | | | | | | | |
|---|---|---|---|---|---|---|---|---|
| Calculated: | % C | 59.26 | % H | 7.01 | % N | 6.28 | % Cl | 23.85 |
| Found: | | 59.2 | | 7.0 | | 6.3 | | 23.6 |

EXAMPLE 13

[4aRS(4aα, 8α, 8aα)](±)-1-[2-(3,4-dichlorophenyl)-1-oxopropyl]-decahydro-8-(1-pyrrolidinyl)-quinoline hydrochloride (isomer B)

570 mg of α-methyl-3,4-dichlorophenyl acetic acid and 417 mg of the product of Step C of Example 1 in 5 ml of methylene chloride were stirred for 40 hours at ambient temperature in the presence of 20 mg of 4-dimethylamino-pyridine and 635 mg of dicyclohexylcarbodiimide. The dicyclohexylurea formed was filtered off and the filtrate was concentrated to dryness under reduced pressure. The residue was taken up in 50 ml of ether, washed with a saturated aqueous solution of sodium bicarbonate, then with water and dried. The solvents were eliminated under reduced pressure and the residue was taken up in ether and the crystallized product was separated. The mother liquors of crystallization were concentrated to dryness to obtain 905 mg of crude product which was chromatographed over silica (eluent:ethyl acetate with 2% of triethylamine) to obtain 378 mg of isomer A and 303 mg of isomer B in the form of a base. 287 of the isomer B base were dissolved in 1 ml of ether, then filtered and rinsed with ether and with ethanol. 0.5 ml of a 5.75N ethanol solution of hydrochloric acid were added to the filtrate which was concentrated under reduced pressure to a volume of 0.5 ml, 10 ml of ether were added and the crystallized product was separated and dried at 70° C. under reduced pressure to obtain 146 mg of [4aRS(4aα, 8α, 8aα)](±)-1-[2-(3,4-dichlorophenyl)-1-oxopropyl]-decahydro-8-(1-pyrrolidinyl)-quinoline hydrochloride (isomer B) melting at ≈254° C. (decomposes).

| Analysis: $C_{22}H_{30}Cl_2N_2O$, HCl; molecular weight = 445.863 | | | | | | | | |
|---|---|---|---|---|---|---|---|---|
| Calculated: | % C | 59.26 | % H | 7.01 | % N | 6.28 | % Cl | 23.85 |
| Found: | | 59.3 | | 7.0 | | 6.3 | | 23.7 |

EXAMPLE 14

[4aRS(4aα, 8α, 8aα)](±)-1-[(benzo[b]-thien-4-yl)-acetyl]-decahydro-8-(1-pyrrolidinyl)-quinoline hydrochloride Using the procedure of Example 8, 500 mg of 4-thianaphthalene acetic acid were reacted with stirring for 6 hours to obtain 655 mg of [4aRS(4aα, 8α, 8aα)](±)-1-[(benzo[b-thien-4yl)-acetyl]-decahydro-8-(1-pyrrolidine)-quinoline hydrochloride melting at >260° C.

EXAMPLE 15

[4aRS(4aα, 8α, 8aα)](±)-1-[(1H-indol-3-yl)-acetyl]-decahydro-8-(1-pyrrolidinyl)-quinoline fumarate Using the procedure of Example 8, 455 mg of 3-indole-acetic acid were reacted with stirring for 40 hours and the fumarate was prepared by the procedure of Example 4 crystallizing from methanol 233 mg of the [4aRS(4aα, 8α, 8aα)](±)-1-(1H-indol-3-yl)-acetyl]-decahydro-8-(1-pyrrolidinyl)-quinoline fumarate melting at >260° C.

| Analysis: $C_{23}H_{31}N_3O.\frac{1}{2} C_4H_4O_4$; molecular weight = 423.560 | | | | | | |
|---|---|---|---|---|---|---|
| Calculated: | % C | 70.89 | % H | 7.85 | % N | 9.92 |
| Found: | | 70.8 | | 8 | | 9.8 |

EXAMPLE 16

[4aRS(4aα, 8α, 8aα)](±)-1-(phenyl-acetyl)-decahydro-8-(1-pyrrolidinyl)-quinoline fumarate Using the procedure of Example 14, 442 mg of phenyl acetic acid, 527 mg of carbonyldiimidazole and 521 mg of the product prepared in Step C of Example 1 were reacted with stirring for 16 hours to obtain 641 mg of [4aRS(4aα, 8α, 8aα)](±)-1-(phenyl-acetyl)-decahydro-8-(1-pyrrolidinyl)-quinoline fumarate which after crystallization from ethanol melted at 228° C.

| Analysis: $C_{21}H_{30}N_2O$; molecular weight = 442.56 | | | | | | |
|---|---|---|---|---|---|---|
| Calculated: | % C | 67.85 | % H | 7.74 | % N | 6.35 |
| Found: | | 67.8 | | 7.8 | | 6.3 |

EXAMPLE 17

[4aRS(4aα, 8α, 8aα)](±)-1-[(4-methylphenyl)-acetyl]-decahydro-8-(1-pyrrolidinyl)-quinoline fumarate Using the procedure of Example 8, 390 mg of p-tolyl-acetic acid were reacted with stirring for 6 hours and the product obtained in the form of a base was converted into a fumarate by the method of Example 4. After crystallization from isopropanol, 458 mg of [4aRS(4aα, 8α, 8aα)](±)-1-[(4-methylphenyl)-acetyl]-decahydro-8-(1-pyrrolidinyl)-quinoline fumarate melting at 198° C. were obtained.

| Analysis: $C_{22}H_{32}N_2O.1.5 C_4H_4O_4$; molecular weight = 514.624 | | | | | | |
|---|---|---|---|---|---|---|
| Calculated: | % C | 65.35 | % H | 7.44 | % N | 5.4 |
| Found: | | 65.1 | | 7.5 | | 5.3 |

| Analysis: $C_{23}H_{30}N_2OS.HCl$; molecular weight = 419.032 | | | | | | | | |
|---|---|---|---|---|---|---|---|---|
| Calculated: | % C | 65.93 | % H | 7.46 | % N | 6.68 | % S | 7.65 | % Cl | 8.46 |
| Found: | | 65.8 | | 7.6 | | 6.6 | | 7.3 | | 8.7 |

EXAMPLE 18

[4aRS(4aα, 8α, 8aα)](±)-1-[(4-pyridinyl)-acetyl]-decahydro-8-(1-pyrrolidinyl)-quinoline fumarate Using the procedure of Example 8, 452 mg of 4-pyridyl-acetic acid were reacted with stirring for 3 hours and the product obtained in the form of a base was converted into fumarate by the method of Example 4 to obtain 373 mg of [4aRS(4aα, 8α, 8aα)](±)-1-(4-pyridinyl)-acetyl]-decahydro-8-(1-pyrrolidinyl)-quinoline fumarate melting at 232° C.

| Analysis: $C_{20}H_{29}N_3O.1.5\ C_4H_4O_4$; molecular weight = 501.585 | | | | | | | |
|---|---|---|---|---|---|---|---|
| Calculated: | % C | 62.26 | % H | 7.03 | % N | 8.38 |
| Found: | | 62.2 | | 7.1 | | 8.4 |

EXAMPLE 19

[4aRS(4aα, 8α, 8aα)](±)-1-(2-thienyl-acetyl)-decahydro-8-(1-pyrrolidinyl)-quinoline fumarate Using the procedure of Example 13, 512 mg of thiophene-acetic acid, 521 mg of the product prepared as at Step C of Example 1, 816 mg of dicyclohexylcarbodiimide and 10 mg of 4-dimethylaminopyridine were reacted and after 42 hours of stirring at ambient temperature, the product was obtained in the form of the base which was converted into fumarate by the method of Example 4 to obtain 648 mg [4aRS(4aα, 8α, 8aα)](±)-1-(2-thienyl-actyl)-decahydro-8-(1-pyrrolidinyl)-quinoline fumarate melting at 252° C. (decomposes).

| Analysis: $C_{19}H_{28}N_2OS, C_4H_4O_4$; molecular weight = 448.585 | | | | | | | | | |
|---|---|---|---|---|---|---|---|---|---|
| Calculated: | % C | 61.58 | % H | 7.19 | % N | 6.24 | % S | 7.15 |
| Found: | | 61.5 | | 7.3 | | 6.2 | | 7.02 |

EXAMPLE 20

[4aRS(4aα, 8α, 8aα)](±)-1-(3,4,5-trimethoxybenzoyl)-decahydro-8-(1-pyrrolidinyl)-quinoline hydrochloride 510 mg of 3,4,5-trimethoxybenzoyl chloride and 417 mg of the product of Step C of Example 1 were reacted in ether for 40 hours at ambient temperature and the crude product obtained in the form of the base was converted into the hydrochloride as in Example 1 to obtain 319 mg of the expected product melting at ≈260° C.

| Analysis: $C_{23}H_{34}N_2O_4.HCl$; molecular weight = 438.999 | | | | | | | | | |
|---|---|---|---|---|---|---|---|---|---|
| Calculated: | % C | 62.93 | % H | 8.04 | % N | 6.38 | % Cl | 8.07 |
| Found: | | 62.7 | | 8.1 | | 6.3 | | 8.0 |

EXAMPLE 21

[4aRS(4aα, 8α, 8aα)](±)-1-(4-bromobenzoyl)-decahydro-8-(1-pyrrolidinyl-quinoline fumarate Using the procedure of Example 20, 483 mg of bromobenzoyl chloride were reacted with stirring for 22 hours at ambient temperature. The crude product obtained in the form of the base was converted into the fumarate by the method of Example 4 to obtain 457 mg of [4aRS(4aα, 8α, 8aα)](±)-1-(4-bromobenzoyl)-decahydro-8-(1-pyrrolidinyl)-quinoline fumarate melting at 206° C. (decomposes).

| Analysis: $C_{20}H_{27}BrN_2O.C_4H_4O_4$; molecular weight = 507.434 | | | | | | | | | |
|---|---|---|---|---|---|---|---|---|---|
| Calculated: | % C | 56.80 | % H | 6.16 | % N | 5.52 | % Br | 15.74 |
| Found: | | 56.6 | | 6.2 | | 5.5 | | 15.6 |

EXAMPLE 22

[4aRS,(4aα, 8α, 8aα)](±)-1-(3,4-dichlorobenzoyl)-decahydro-8-(1-pyrrolidinyl)-quinoline fumarate Using the procedure of Example 20, 461 mg of 3,4-dichlorobenzoyl chloride were reacted with stirring for 20 hours at ambient temperature and the crude product obtained in the form of a base was converted into the fumarate by the method of Example 4 to obtain 547 mg of [4aRS(4aα, 6α, 8aα)](±)-1-(3,4-dichlorobenzoyl)-decahydro-8-(1-pyrrolidinyl)-quinoline fumarate melting at 202° C.

| Analysis: $C_{20}H_{26}Cl_2N_2O, C_4H_4O_4$; molecular weight = 497.423 | | | | | | | | | |
|---|---|---|---|---|---|---|---|---|---|
| Calculated: | % C | 57.95 | % H | 6.08 | % N | 5.63 | % Cl | 14.25 |
| Found: | | 57.7 | | 6.2 | | 5.6 | | 14.1 |

EXAMPLE 23

[4aRS(4aα, 8α, 8aα)](±)-1-[(3,4-dichlorophenyl)-acetyl]-decahydro-8-dimethylamino quinoline hydrochloride

STEP A:

N,N-dimethyl-5,6,7,8-tetrahydro-8-quinolinamine 4.08 g of 8-chloro-5,6,7,8-tetrahydroquinoline hydrochloride of Example 1 were mixed with stirring for 75 minutes in 20 ml of a 40% aqueous solution of dimethylamine and the mixture was heated for 1 hour at 65° C.±2° C., then allowed to cool to ambient temperature. The reaction medium was saturated with sodium chloride and 0.3 ml of 2N sodium hydroxide were added. After extracting with ether, the extracts were washed with water, dried, and the solvent was eliminated under reduced pressure to obtain 3.35 g of N,N-dimethyl-5,6,7,8-tetrahydro-8-quinolinamine which was used as is for the following step.

STEP B: [4aRS(4aα, 8α, 8aα)]-N,N-dimethyl-decahydro-8-quinolinamine (isomer cis A) and [4aRS(4aα, 8α, 8aα)](±) N,N-dimethyl-decahydro-8-quinolinamine (isomer cis B)

(1) Catalytic Reduction 3.35 g of the product of Step A, 33 ml of methanol and 3.3 ml of hydrochloric acid were introduced into a hydrogenation apparatus in the presence of 0.37 g of 80% platinum oxide and hydrogenation was continued for 7 hours at 22° to 24° C. at a pressure of 1840 mbars. The catalyst was filtered off, and after rinsing and concentrating to dryness under reduced pressure, 4.85 g of [4aRS(4aα, 8α, 8aβ)](±)-N,N-dimethyl-decahydro-8-quinolinamine (isomer cis B) were obtained.

(2) Crystallization of the Hydrochloride of the Isomer Cis A

The dried extract was taken up in 15 ml of isopropanol, and crystallization was initiated. After standing for 1 hour at ambient temperature, the crystals were filtered off, rinsed with isopropanol and with ether, then dried under reduced pressure at 50° C. After crystallization from ethanol, 1.27 g of the expected product were recovered in the form of the hydrochloride melting at >260 ° C.

(3) Return to the Base 1.237 g of the said product were dissolved in 5 ml of water which was then saturated with sodium chloride and 2 ml of 2N sodium hydroxide were added. Extraction was done with ether and the extracts were dried and the solvent was eliminated under reduced pressure to obtain 0.962 g of the expected product in the form of the base.

(4) Preparation of the Cis B Isomer

The combined mother liquors of crystallization of the hydrochloride of the cis A isomer were concentrated to dryness under reduced pressure and the residue was taken up in 10 m of water, saturated with sodium chloride and alkalized with 2N sodium hydroxide. Extraction was done with ether and the extracts were dried and the solvent was eliminated under reduced pressure. After chromatography over silica (eluent:ethyl acetate - methanol - triethylamine 85-10-5), 384 mg of the expected product were recovered.

STEP C: [4aRS(4aα, 8α, 8aα)](±)-1-[(3,4-dichlorophenyl)-acetyl]-decahydro-8-dimethylamino quinoline 1.160 g of dicyclohexylcarbodiimide were added to a solution of 855 mg of the cis A isomer in the form of the base of Step B (3) and 1.160 g of 3,4-dichlorophenyl acetic acid in 15 ml of methylene chloride. The mixture was stirred for 18 hours and the urea formed was eliminated by filtering. The filtrate was concentrated to dryness under reduced pressure and the residue was taken up in 50 ml of ether, washed with a saturated aqueous solution of sodium bicarbonate, and extracted with ether. The extracts were dried and the solvent was eliminated under reduced pressure to obtain 2.5 g of product in the form of the base which was dissolved in 15 ml of ethanol. 2 ml of a 5.75N solution in ethanol of hydrochloric acid were added, and crystallization was allowed for 1 hour. The crystals were filtered off and dried, rinsed with ethanol and then with ether and dried at 50° C. under reduced pressure to obtain 1.064 g of [4aRS(4aα,8α, 8aα)](±)-1-[(3,4-dichlorophenyl)-acetyl]-decahydro-8-dimethylamino quinoline melting at ≈256° C.

| Analysis: $C_{19}H_{26}Cl_2N_2O$, HCl; molecular weight = 405.798 | | | | |
|---|---|---|---|---|
| Calculated: | % C 56.24 | % H 6.70 | % N 6.90 | % Cl 26.21 |
| Found: | 56.1 | 6.7 | 6.8 | 25.8 |

EXAMPLE 24

[4aRS(4aα, 8α, 8aα)](±)-1-[3,4-dichlorophenyl)-acetyl]-decahydro-8-dimethylamino-quinoline oxalate Using the procedure of Step C of Example 23, 844 mg of the isomer cis B prepared at Step B (4) of Example 23 were reacted to obtain 2.065 g of product in the form of the base. 1.22 g of this base and 0.7 g of dihydrated oxalic acid were dissolved in 5 ml of ethanol, then filtered, rinsed with ethanol, and 30 ml of ether were added to the filtrate. The crystals were separated, rinsed with an ethanol-ether (1-3) mixture and then with ether, and dried under reduced pressure at 70° C. to obtain 1.132 g of [4aRS(4aα, 8α, 8aα)](±)-1-1-[3,4-dichlorophenyl)-acetyl]-decahydro-8-dimethylamino-quinoline oxalate melting at 159° C.

| Analysis: $C_{19}H_{26}Cl_2N_2O$; molecular weight = 459.373 | | | | |
|---|---|---|---|---|
| Calculated: | % C 54.90 | % H 6.14 | % N 6.10 | % Cl 15.44 |
| Found: | 54.8 | 6.0 | 6.9 | 15.2 |

EXAMPLE 25

[4aRS(4aα, 8α, 8aα)](±)-1-]3,4-dichlorophenyl)-acetyl]-decahydro-8-(1-piperidinyl)-quinoline hydrochloride

STEP A: 8-(1-piperidinyl)-5,6,7,8-tetrahydroquinoline 3.9 ml of piperidine were introduced into a solution of 2 g of 8-chloro-5,6,7,8-tetrahydroquinoline hydrochloride in 5 ml of water and the mixture was stirred for 15 minutes, heated for two-and-a-half hours at 57°±2° C., then cooled to ambient temperature. The medium was saturated with sodium chloride and extracted with ether. The solvent was eliminated under reduced pressure to obtain 2.07 g of 8-(1-piperidinyl)-5,6,7,8-tetrahydroquinoline.

STEP B: [4aRS(4aα, 8α, 8aα)](±)-decahydro-8-(1-piperidinyl)-quinoline (isomer cis A); [4aRS(4aα, 8β, 8aα)](±)-decahydro-8-(1-piperidinyl)-quinoline (isomer cis B) and [4aRS(4aα, 8α, 8aβ)](±)-decahydro-8-(1-piperidinyl-quinoline (isomer trans A)

1.974 g of the product of Step A in 30 ml of ethanol was hydrogenated for 6 hours at a pressure of 1850 mbars and at ambient temperature in the presence of 3 ml of hydrochloric acid and 0.2 g of platinum oxide. The catalyst was filtered off, and the filtrate was rinsed and concentrated to dryness under reduced pressure. The residue was taken up in 10 ml of water and 12 ml of sodium hydroxide were added. Extraction was done with ethyl acetate and the extracts were dried and the solvent was eliminated under reduced pressure to obtain 2.04 g of crude product which was chromatographed over silica (eluent : ethyl acetate - methanol - triethylamine 85-10-5) to obtain 551 mg of isomer cis A, 733 mg of isomer cis B and 353 mg of isomer trans A.

STEP C: [4aRS(4aα, 8α, 8aα)](±)-1-[3,4-dichlorophenyl)-acetyl]-decahydro-8-(1-piperidinyl)-quinoline hydrochloride 479 mg of 3,4-dichlorophenyl-acetic acid and 467 mg of cis A isomer of Step B were reacted for 6 hours in 7.2 ml of methylene chloride in the presence of 482 mg of dicyclohexylcarbodiimide and the dicyclohexylurea formed was filtered off. The filtrate was concentrated to dryness under reduced pressure, and the residue was taken up in 30 ml of ethyl acetate. The organic phase was washed with a saturated aqueous solution of sodium bicarbonate, then with water, then dried, and the solvent was eliminated under reduced pressure to obtain 1.117 g of crude product in the form of the base which was converted into the hydrochloride by the method of Example 1 to obtain 600 mg of [4aRS(4aα, 8α, 8aα)](±)-1-[3,4-dichlorophenyl)-acetyl]-decahydro-8-(1-piperidinyl)-quinoline hydrochloride melting at >260° C.

| Analysis: $C_{22}H_{30}Cl_2N_2O$, HCl; molecular weight = 445.863 | | | | | | | | | |
|---|---|---|---|---|---|---|---|---|---|
| Calculated: | % C | 59.26 | % H | 7.01 | % N | 6.28 | % Cl | 23.85 |
| Found: | | 59.4 | | 7.2 | | 6.2 | | 24.0 |

EXAMPLE 26

[4aRS(4aα, 8β, 8aα)](±)-1-(3,4-dichlorophenyl)-acetyl]-decahydro-8-(1-piperidinyl)-quinoline fumarate Using the procedure of Step C of Example 25, 550 mg of 3,4-dichlorophenyl-acetic acid and 537 mg of cis B isomer of Step B of Example 25 were reacted with stirring for 20 hours at ambient temperature to obtain 1.296 g of crude product in the form of the base which was converted into the fumarate as in Example 4 to obtain 202 mg of [4aRS (4α, 8β, 8aα)](±)-1-[(3,4-dichlorophenyl)-acetyl]-decahydro-8-(1-piperidinyl)-quinoline fumarate melting at ≈227° C.

| Analysis: $C_{22}H_{30}Cl_2N_2O$, $C_4H_4O_4$; molecular weight = 525.177 | | | | | | | | | |
|---|---|---|---|---|---|---|---|---|
| Calculated: | % C | 59.43 | % H | 6.52 | % N | 5.33 | % Cl | 13.49 |
| Found: | | 59.3 | | 6.8 | | 5.1 | | 13.5 |

EXAMPLE 27

[4aα, 8α, 8aα)](±)-1-[1-[(3,4-dichlorophenyl)-acetyl]-decahydro-8-quinolenyl]-1-methyl-pyrrolidinium bromide 6 g of methyl bromide were added to a solution of 401 mg of the product of Example 1 in the form of the base in 6 ml of tetrahydrofuran and the mixture was stirred for 24 hours at ambient temperature, then separated. The crystallized product was rinsed with tetrahydrofuran, then with ether, and dried under reduced pressure at 70° C. to 80° C. to obtain 455 mg of [4aRS(4aα, 8α, 8aα)](±)-1-[(3,4-dichlorophenyl)-acetyl]-decahydro-8-quinolenyl]-1-methyl-pyrrolidinium bromide melting at ≈170° C.

| Analysis: $C_{22}H_{31}BrCl_2N_2O$; molecular weight = 490.319 | | | | | | | | | | | |
|---|---|---|---|---|---|---|---|---|---|---|---|
| Calculated: | % C | 53.89 | % H | 6.37 | % N | 5.71 | % Cl | 14.46 | % Br | 16.3 |
| Found: | | 53.8 | | 6.5 | | 5.5 | | 13.7 | | 14.9 |

EXAMPLE 28

Tablets were prepared containing 200 mg of product of Example 1 and sufficient excipient of lactose, talc, starch, magnesium stearate for a final weight of 800 mg.

EXAMPLE 29

An injectable solution (intramuscular route) was prepared containing 50 mg of the product of Example 1 and sufficient sterile solvent q.s. for 5 ml.

PHARMACOLOGICAL STUDY (1) Bond with the Opiate Receptor K in Vitro

Membrane residues were used kept at −30° C. for about 30 days, and prepared from the cerabella of guinea-pigs. These residues were put back into suspension in Tris buffer pH 7.7 and 2 ml fractions were distributed in hemolysis tubes and $9^3H$ ethylketo-cyclazocine InM and the product under test were added. The product was first tested at $5 \times 10^{-6}M$ (in triplicate). When the product tested displaced by more than 50%, the radioactivity bonded specifically to the receptor, it was tested again over a range of 7 doses to determine the dose which inhibited by 50% the radio-activity bonded specifically to the receptor. In this way, the 50% inhibiting concentration was determined.

The non-specific bonding was determined by the addition of the product known under the name U-50488 H at $10^{-5}M$ (in triplicate). After incubating at 25° C. for 40 minutes, returning to the water-bath at 0° C. for 5 minutes, filtering under vacuum, and rinsing with Tris buffer pH 7.7, the radio-activity was counted in the presence of scintillating Trition. The result were expressed directly as the 50% inhibiting concentration ($IC_{50}$), that is to say, in concentration of the product studied, expressed in nM, necessary in order to displace 50% of the specific radio-activity fixed on the receptor studied. The results are in the following Table.

| Product of example | $IC_{50}$ in nM |
|---|---|
| 1 | 2.7 |
| 6 | 5 |
| 7 | 9.5 |
| 8 | 17 |
| 10 | 12 |
| 11 | 6 |
| 12 | 5.4 |
| 14 | 4.1 |
| 22 | 7.4 |

(2) Analgesic Activity

Hot plate test

Female mice weighing 22 to 24 g were placed one by one on a copper plate maintained at 56° C. and the reaction to the pain was shown by the animal licking its front paws. The time of this reaction was noted and only the mice reacting in less than 8 seconds were retained. The animals were distributed in homogeneous groups and treated with the product under study administered sub-cutaneously, one group receiving only the vehicle. The time of reaction to the pain was again measured 30 to 60 minutes after the treatment and the active dose, or $AD_{100}$ which is the dose which increased the reaction time by 100%, 30 minutes after the treatment, taking account of the variations in the reaction time of the control animals was determined. For the product of Example 1, the $AD_{100}$ was 20 mg/kg.

Stretchings Test

The test employed was based on the fact remarked by Koster et al [Fed. Proc., 1959, 1B, 412] according to which the intraperitoneal injection of acetic acid in mice caused repeated movements of stretching and twisting which can persist for more than 6 hours. Analgesics prevent or diminish this syndrome which can be consisered as the exteriorization of a diffuse abdominal pain. A 1% solution of acetic acid in water was used and the dose which in these conditions caused the syndrome was 0.01 ml per g, or 100 mg/kg of acetic acid. The product studied was administered orally half-an-hour before the acetic acid injection, the mice having fasted since the day before the test. The stretching were observed and counted for each mouse during an observation period of 15 minutes beginning immediately after the injection of the acetic acid. The results expressed as the $AD_{50}$, (the dose which enabled a reduction of 50% in the number of stretching in comparison with the control animal) were determined and are reported in the following Table.

| Product example | $DA_{50}$ in mg/kg |
| --- | --- |
| 1 | 18 |
| 6 | 21 |
| 8 | 20 |

(3) Anti-Arrhythmic Action in the Rat

Male rats weighing 300 to 350 g, anaesthetized intraperitoneally with 1.20 g/kg of urethane, were tracheotomized and submitted to an artifical respiration (40–50 breaths of 3 ml per minute). Needles were implanted sub-cutaneously to record the electrocardiogram of the rats on the DII derivation signal and the products under test were administered intravenously. Five minutes after the product was administered, the jugular vein of the rats was perfused with 10 μg/mn from 0.2 ml of a solution of aconitrine and the time of appearance of disturbances of the cardiac rhythm was noted. The results were expressed as a percentage of the extension of the time of appearance of the disturbances of the cardiac rhythm in comparison with controls and as a function of the dosage of the product under test. The results appearing in the following table show that certain of the products of the present application were endowed with good antiarrhythmic properties.

| Product of example | Dose mg/kg | Percentage of extension of time |
| --- | --- | --- |
| 1 | 10 | +113.5 |
|   | 5 | +56.5 |
|   | 2.5 | +31.5 |
|   | 1 | +17.5 |
| 2 | 2.5 | +182 |
|   | 1 | +93 |
|   | 0.5 | +46 |
|   | 0.25 | +26 |

-continued

| Product of example | Dose mg/kg | Percentage of extension of time |
| --- | --- | --- |
| 3 | 10 | +35.5 |
|   | 5 | +36 |
|   | 2.5 | +17 |
| 4 | 10 | +112 |
|   | 1 | +38.5 |
|   | 0.5 | +10.5 |
| 20 | 1 | +141 |
|   | 0.5 | +85 |
|   | 0.25 | +45 |

(4) Test of Asphyxic Anoxia

The study was carried out on male rats (Charles River CDE) weighing 250–300 g, anaesthetized with ether, tracheotomized, paralyzed with d-tubocuranine hydrochloride, 0.5 mg/kg IV, and submitted to artifical respiration with a mixture of 70% of nitrogen protoxide and 30% of oxygen. The body temperature was maintained at 37° C. by an automatic temperature controller. Two silver-silver chloride electrodes were implanted on the cranium and fixed with dental cement in the regions of the visual cortex and the cerebellum, to record the E.E.G. (electroencephalogram). A common carotid artery was catheterized to record the arterial pressure and the cardiac frequency. The values of $paO_2$, $paCO_2$ and of pH were measured before the anoxia and the frequency of the respiratory pump was adjusted in order to obtain the normal values. The anoxia was obtained by disconnecting the respiratory pump, by the technique described by Rosner et al [Arch. Int. Pharmacodyn. 194, 375 (1971)]. After 3 minutes, the respiratory pump was restarted and the ventilation was maintained for 30 minutes. Before the anoxia, at the end of the anoxia and 2, 10 and 30 minutes after restarting the ventilation, the E.E.G. was recorded on an encephalograph and the power spectra of the E.E.G. were analyzed by a PDP 11/34 digital computer. During the recording of the E.E.G., precautions were taken to avoid visual and acoustic stimulations. 5 periods of 10 seconds were selected by visual control each minute to exclude the artifacts and the analysis was made by Fourier transformation. The power spectrum was evaluated between 0 and 25 Hz with a resolution of 0.2 Hz.

The product under test was dissolved in Methocel at 0.5%, and was administered by intravenous route at 1 and 5 mg/kg, 3 minutes before stopping the pump. The values of $paO_2$, $paCO_2$ and of the pH were again measured 30 minutes after the anoxia and the mean arterial pressure (M.A.P.) and the cardiac frequency (C.F.) were recorded. Groups of 10 animals were used and the results are given in Table I.

The total power and the energies of the different frequency bands were expressed as percentages of those recorded during the check before the anoxia. The standard deviations were shown to indicate the dispersion of the data. The Mann Whitney U test was used to calculate the degree of significance of the difference between the controls (physiological serum) and the treated group. ns=$P>0.05$; *=$P<0.05$; **=$P<0.01$. The results obtained with the product of Example 1 are shown in Table I.

TABLE 1

Spectral analysis of electroencephalogram of anaesthetized rats after 3 minutes of asphyxic anoxia.

| Treatment | dose mg/kg i.v. | Before | End of Anoxia | Time in minutes after anoxia 2 | 10 | 30 |
|---|---|---|---|---|---|---|
| DELTA | | | | | | |
| Controls | — | 100 ± 0 | 1 ± 0 | 3 ± 1 | 902 ± 250 | 278 ± 44 |
| Product of example 1 | 5 | 100 ± 0 | 1 ± 0 | 243 ± 68** | 127 ± 25** | 123 ± 14** |
| | 1 | 100 ± 0 | 1 ± 0 | 214 ± 60** | 404 ± 123* | 225 ± 32 |
| THETA | | | | | | |
| Controls | — | 100 ± 0 | 0 ± 0 | 1 ± 0 | 40 ± 7 | 71 ± 5 |
| Product of example 1 | 5 | 110 ± 0 | 0 ± 0 | 6 ± 2** | 63 ± 11 | 94 ± 14* |
| | 1 | 100 ± 0 | 0 ± 0 | 6 ± 2** | 57 ± 8* | 72 ± 6 |
| ALPHA | | | | | | |
| Controls | — | 100 ± 0 | 0 ± 0 | 1 ± 0 | 69 ± 10 | 83 ± 11 |
| Product of example 1 | 5 | 100 ± 0 | 0 ± 0 | 25 ± 5** | 55 ± 4 | 80 ± 8 |
| | 1 | 100 ± 0 | 0 ± 0 | 19 ± 6** | 73 ± 5 | 79 ± 6 |
| BETA | | | | | | |
| Controls | — | 100 ± 0 | 0 ± 0 | 1 ± 0 | 90 ± 11 | 90 ± 10 |
| Product of example 1 | 5 | 100 ± 0 | 0 ± 0 | 33 ± 5** | 103 ± 14 | 102 ± 9 |
| | 1 | 100 ± 0 | 0 ± 0 | 21 ± 7** | 96 ± 11 | 87 ± 5 |
| TOTAL POWER | | | | | | |
| Controls | — | 100 ± 0 | 0 ± 0 | 1 ± 0 | 252 ± 76 | 117 ± 9 |
| Product of example 1 | 5 | 100 ± 0 | 0 ± 0 | 68 ± 14** | 79 ± 6** | 100 ± 8 |
| | 1 | 100 ± 0 | 0 ± 0 | 70 ± 22** | 173 ± 41 | 120 ± 9 |

\* = P < 0,05
\*\* = P < 0,001 (Test of Mann-Whitney U)

Results

The product, administered intravenously at a dose of 5 mg/kg, caused a remarkable anticipation of the recuperation of the electro-cortical activity in all the frequency bands. Thirty minutes after the anoxia, the values of the different bands of frequency of the group treated with 5 mg/kg were almost equal to the base values, while in the controls, there persisted a large slow component (delta band) which indicated that a state of cerebral suffering was still present. Even at a dose of 1 mg/kg, an anticipation of the recuperation of the electro-cortical activity was observed, while the effect on the normalization of the trace was less evident. In fact, after 30 minutes from the end of the anoxia, the value of the delta bands was still about twice the base value.

Various modifications of the products and method of the invention may be made without departing from the spirit or scope thereof and it is to be understood that the invention is intended to be limited only as defined in the appended claims.

We claim:

1. A compound selected from the group consisting of enantiomeric and diastereoisomeric forms of decahydroquinolines of the formula

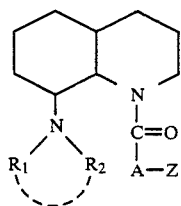

wherein $R_1$ and $R_2$ are individually selected from the group consisting of hydrogen and alkyl of 1 to 5 carbon atoms or taken together with the nitrogen atom to which they are connected form a member selected from the group consisting of piperidinyl unsubstituted or substituted with alkyl or alkoxy of 1 to 5 carbon atoms, A is selected from the group consisting of $>(CH_2)_n>$ and alkylene substituted with an alkyl and having 2 to 8 carbon atoms, n is integer from 0 to 5, Z is selected from the group consisting of phenyl, phenyl substituted with a t least one member of the group consisting of alkyl and alkoxy of 1 to 5 carbon atoms, halogen, $>OH$, $>CF_3$, $>NO_2$, $>NH_2$ and mono and dialkylamino of 1 to 5 alkyl carbon atoms; naphthyl, indenyl, pyridinyl, thienyl, thiazolyl, oxazolyl isoxazolyl, imidazolyl, indolyl, quinolyl, benzofuranyl, benzo[b]-thienyl, benzimidazolyl, benzoxazolyl and benzothiazolyl, unsubstituted or substituted with at least one substituent selected from the group consisting of alkyl and alkoxy of 1 to 5 carbon atoms, $>CF_3$, $>NO_2$, $>NH_2$, mono- and dialkylamino of 1 to 5 alkyl carbon atoms and phenyl unsubstituted or substituted with at least one substituents selected from the group consisting of alkyl and alkoxy of 1 to 5 carbon atoms and halogen and their non-toxic, pharmaceutically acceptable acid addition salts and quaternary ammonium salts.

2. A compound of claim 1 wherein $R_1$ and $R_2$ are methyl or ethyl or together with the nitrogen atom to which they are bonded form pyridinyl, A is either $(CH_2)_n$ wherein n is 0 or 1 or 1,1-ethanedilyl, Z is selected from the group consisting of phenyl, naphthyl, indenyl, pyridinyl, thienyl, thiazolyl, oxazolyl, isoxazolyl, imidazolyl, indolyl, quinolyl, benzofurany, benzo[b]-thienyl, benzimidazolyl, and benzothiazolyl, unsubstituted or substituted with at least one substituent.

3. An analgesic composition comprising an analgesically effective amount of at least one compound of claim 1 and an inert pharmaceutical carrier.

4. A composition of claim 3 wherein in the compound $R_1$ and $R_2$ are methyl or ethyl or together with the nitrogen atom to which they are bonded form pyridinyl, A is either $(CH_2)_n$ wherein n is 0 or 1 or 1,1-ethanediyl, Z is selected from the group consisting of phenyl, naphthyl, indenyl, pyridinyl, thienyl, thiazolyl, oxazolyl, isoxazolyl, imidazolyl, indolyl, quinolyl, benzofuranyl, benzo[b]-thienyl, benzimidazolyl, benzoxazolyl and benzothiazolyl, unsubstituted or substituted with one or more substituents.

5. A method of inducing analgesic activity in warm-blooded animals comprising administering to warm-blooded animals an analgesically effective amount of at least one compound of claim 1.

6. A method of claim 5 wherein in the compound $R_1$ and $R_2$ are methyl or ethyl or together with the nitrogen atom to which they are bonded form pyridinyl, A is either $(CH_2)_n$ wherein n is 0 or 1 or 1,1-ethanediyl, Z is selected from the group consisting of phenyl, naphthyl, indenyl, pyridinyl, thienyl, thiazolyl, oxazolyl, isoxazolyl, imidazolyl, indolyl, quinolyl, benzofuranyl, benzo[b]-thienyl, benzimidazolyl, benzoxazolyl and benzothiazolyl, unsubstituted or substituted with one or more substituents.

* * * * *